(12) United States Patent
Williams

(10) Patent No.: US 11,590,021 B2
(45) Date of Patent: Feb. 28, 2023

(54) FEMININE COOLING APPARATUS AND METHOD

(71) Applicant: Kesha Williams, Cincinnati, OH (US)

(72) Inventor: Kesha Williams, Cincinnati, OH (US)

( * ) Notice: Subject to any disclaimer, the term of this patent is extended or adjusted under 35 U.S.C. 154(b) by 857 days.

(21) Appl. No.: 16/503,842

(22) Filed: Jul. 5, 2019

(65) Prior Publication Data

US 2020/0008974 A1 Jan. 9, 2020

Related U.S. Application Data

(60) Provisional application No. 62/694,505, filed on Jul. 6, 2018.

(51) Int. Cl.
*A61F 7/00* (2006.01)

(52) U.S. Cl.
CPC ........ *A61F 7/007* (2013.01); *A61F 2007/005* (2013.01); *A61F 2007/0064* (2013.01); *A61F 2007/0075* (2013.01)

(58) Field of Classification Search
CPC ................ A61F 7/007; A61F 2007/005; A61F 2007/0064; A61F 2007/0075
See application file for complete search history.

(56) References Cited

U.S. PATENT DOCUMENTS

| | | |
|---|---|---|
| 4,240,436 A | 12/1980 | Singleton |
| 4,846,824 A | 7/1989 | Lassen et al. |
| 5,167,655 A | 12/1992 | McCoy |
| 5,365,739 A | 11/1994 | Fetterly |
| 5,704,223 A | 1/1998 | MacPherson et al. |
| 6,260,360 B1 | 7/2001 | Wheeler |
| 6,308,341 B1 | 10/2001 | Shelton |
| 6,409,713 B1 | 6/2002 | Osborn, III et al. |
| 6,895,762 B1 * | 5/2005 | Lin ..................... F25B 21/02 62/3.6 |
| 7,231,771 B2 | 6/2007 | McMurry et al. |
| 7,278,270 B2 | 10/2007 | Culp et al. |
| 8,247,637 B2 | 8/2012 | Renzin et al. |
| D694,420 S | 11/2013 | Cole |
| 8,887,512 B2 | 11/2014 | Olsen et al. |
| D764,675 S * | 8/2016 | Peisner ..................... D24/207 |
| 9,962,286 B2 * | 5/2018 | Mahon ..................... A61F 7/10 |
| 10,299,525 B1 | 5/2019 | Buckman |

(Continued)

*Primary Examiner* — Steven O Douglas
(74) *Attorney, Agent, or Firm* — Ronald J. Richter; Nesbitt IP LLC

(57) ABSTRACT

An apparatus for providing prolonged topical cooling to the external female genitalia as a therapeutic benefit to and relief from female itching and burning is disclosed as a lightweight, portable cooling unit in combination with one or more labial inserts which are specifically designed to conform to the user's anatomy. The cooling unit is typically a container capable of both cooling and transporting the labial inserts during travel, and providing easy access to relief when needed by the user. A cooled labial insert can be applied to the external female genitalia for treatment of the acute symptoms associated with vulvar inflammation and irritation. The inventive apparatus can maintain a cooling temperature to the affected area for an extended period of time, limited only by the life of the cooling power source. The labial inserts can be worn in public with minimum disruption to the user's clothing and mobility.

18 Claims, 3 Drawing Sheets

(56) References Cited

U.S. PATENT DOCUMENTS

| | | |
|---|---|---|
| 2005/0004429 A1 | 1/2005 | Tracanna |
| 2005/0137557 A1 | 6/2005 | Swiecicki et al. |
| 2007/0021809 A1 | 1/2007 | Cole et al. |
| 2009/0049845 A1 | 2/2009 | McStravick et al. |
| 2015/0282980 A1* | 10/2015 | Ogunleye ................ A61F 7/10 607/108 |
| 2019/0358440 A1* | 11/2019 | Jackson .................... A61F 7/08 |

* cited by examiner

FEMININE COOLING APPARATUS AND METHOD

CROSS-REFERENCE TO RELATED APPLICATION

This application claims the benefit of U.S. Provisional Application No. 62/694,505, filed Jul. 6, 2018, the disclosure of which is hereby incorporated by reference in its entirety.

FIELD OF THE INVENTION

The present invention relates in general to portable cooling devices, and in particular to a lightweight and portable cooling unit for transporting one or more labial inserts for therapeutic application to the external female genitalia.

BACKGROUND OF THE INVENTION

There are many medical conditions that may cause irritation and inflammation of the female external genitalia, or vulva, which includes the female urethra, the clitoris, and the labia (minor and majora). Such irritation and inflammation is often caused by acidic vaginal secretions deposited on the vulva, or by direct irritation of this delicate tissue by such things as excessive exposure to perspiration, tight undergarments or clothing, or mild trauma from excessive sexual activity. Common acute symptoms include itching, burning, irritation, liquid discharge, odor, or combinations of these. Itching and irritation can also be caused by a vaginal infection, such as a yeast infection (e.g. *Candidiasis*), bacterial vaginosis, or parasitic trichomoniasis. Other conditions such as recent child birth can cause similar acute symptoms of inflammation, burning and overall discomfort.

While steroid creams, medicated pads and other topical medications are often prescribed to treat vulvar burning and inflammation, there is often a delay from the time treatment is begun until relief from the itching and burning is experienced. For example, it can day several days or even weeks before ultimate relief from a yeast infection occurs, during which time the acute symptoms persist. Further, topical creams and the like can be messy to use, and can stain undergarments. If the affected person is out in public, such messy creams and pads can affect clothing appearance as well as that person's mobility, which can be inconvenient and embarrassing. Indeed, women suffering from acute vulvar burning and itching often want immediate and non-messy relief, but to date have had nothing to turn to.

In light of the above, it would be useful to provide a portable and reliable cooling insert and method for treatment of vulvar itching, burning and inflammation. It would also be desirable to provide non-messy relief in the form of a labial insert that can be easily cooled, stored and transported by the user in a small portable cooling unit for an extended period of time, including periods without power.

SUMMARY OF THE INVENTION

Accordingly, the present invention relates to a lightweight, portable cooling unit and one or more associated labial insert(s) which can provide immediate relief of burning and itching of the female external genitalia. The portable cooling unit is in the form of a container having an internal compartment which can cool one or more labial inserts, and each insert has a surface which can be applied to the external female genitalia to maintain a controlled and soothing temperature to the affected area for an extended period of time, limited only by the life of the cooling container power source. A properly cooled labial insert can be applied by a user and worn in public for cooling relief with minimum disruption to the user's clothing and mobility.

A first aspect of the invention provides an apparatus for providing immediate relief from burning and itching of the female external genitalia, the apparatus comprising: (a) a cooling unit; and (b) one or more labial inserts, wherein the cooling unit is portable and operable to cool the one or more labial inserts to a desired target temperature, and wherein each of the one or more labial inserts can be applied to the external female genitalia of a user to maintain a controlled temperature to the affected area for an extended period of time.

A second aspect of the invention provides an apparatus for providing immediate relief from burning and itching of the female external genitalia, the apparatus comprising: (a) a cooling unit, wherein the cooling unit comprises: (i) an upper housing for accommodating: (1) a cooling compartment for receiving the one or more labial inserts; (2) an insulating tray; and (3) a rubber sealing layer, wherein the cooling compartment is seated within the insulating tray and the rubber sealing layer is placed between the upper housing and the cooling compartment; (ii) a base housing for accommodating: (1) inlet air vents; (2) outlet air vents; and (3) a fan; and (iii) a thermoelectric heat transfer module for placement between the upper housing and the base housing, wherein the heat transfer module is in thermally conductive communication with the cooling compartment, and wherein the base housing is reversibly secured to the upper housing with the thermoelectric heat transfer module secured in between; and (b) one or more labial inserts, wherein each of the one or more labial inserts includes: (i) a top contact surface for contacting the female external genitalia, wherein the top contact surface includes a ridge raised above the level of the flange, the ridge including a rounded crest at the highest point above the flange, a first tapered portion sloping from the rounded crest towards the anterior end of the flange, and a second tapered portion sloping from the rounded crest towards the posterior end of the flange; and (ii) a bottom surface defining a flange having an anterior end and a posterior end, wherein the flange has a curvature from the anterior end to the posterior end in order to conform to the user's anatomy, wherein the cooling unit is portable and operable to cool the one or more labial inserts to a desired target temperature, and wherein each of the one or more labial inserts can be applied to the external female genitalia of a user to maintain a controlled temperature to the affected area for an extended period of time.

A third aspect of the invention provides a method for providing immediate relief of female burning and itching, the method comprising: (a) providing an apparatus for both cooling and transporting one or more labial inserts, the apparatus comprising: (i) a cooling unit; and (ii) one or more labial inserts, wherein each of the one or more labial inserts includes a top contact surface for contacting the female external genitalia; (b) cooling the one or more labial inserts to a desired target temperature within the cooling unit; (c) removing one of the one or more labial inserts from the cooling unit when it reaches the desired target temperature; and (d) inserting one of the cooled one or more labial inserts between a user's labia majora so that the top contact surface makes contact with the external female genitalia of a user to maintain a controlled temperature to the external genitalia for an extended period of time.

The nature and advantages of the present invention will be more fully appreciated from the following drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

As used herein, the term "anterior" in reference to human anatomy means the direction towards the front of the wearer during use, and the term "posterior" refers to the direction towards the back of the wearer during use.

The term "top surface" in reference to the inventive labial insert means a surface that is facing generally towards the wearer during use, and which comes into contact with inflamed labial tissues. The term "bottom surface" refers to a surface facing generally away from the wearer during use.

Figure 1:
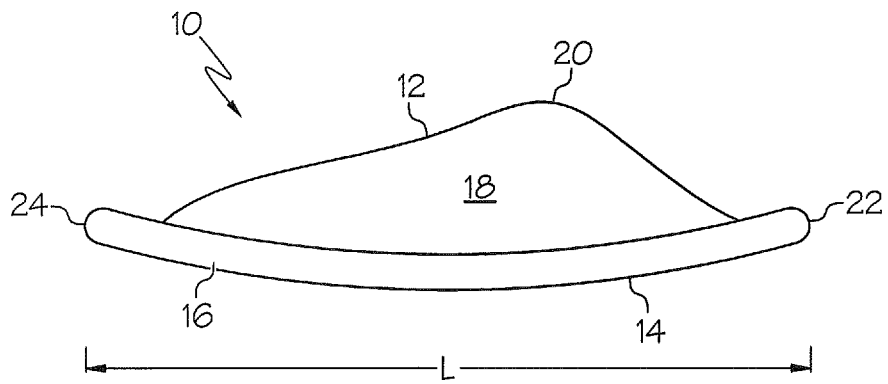
FIG. 1 is a side view of a preferred embodiment of a labial insert according to the present invention.
Figure 2:
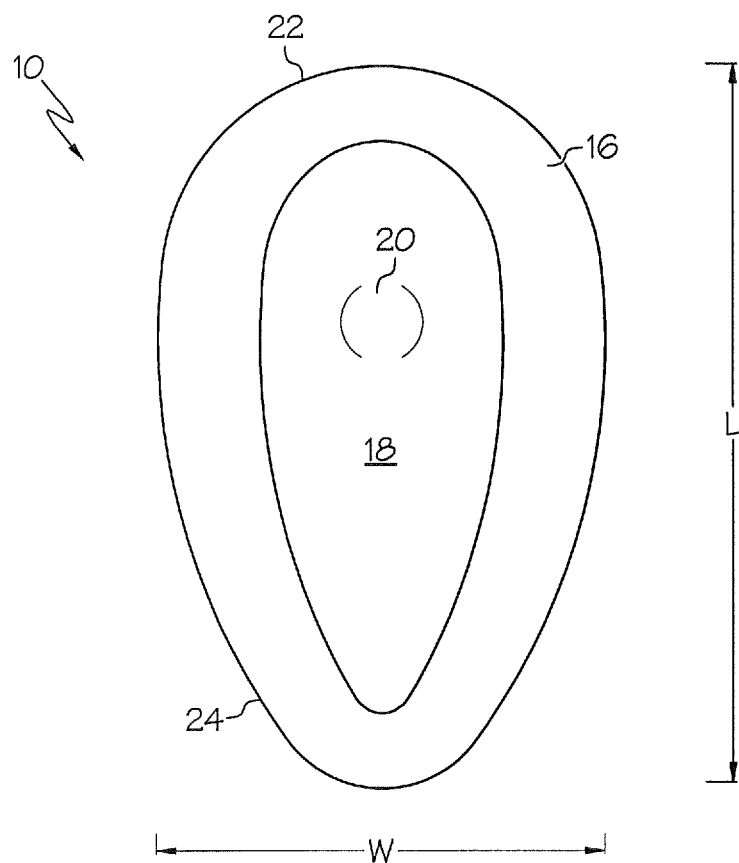
FIG. 2 is a top view of the labial insert of FIG. 1.

As generally illustrated in FIGS. 1 and 2, a preferred embodiment of the inventive labial insert 10 is configured to cooperate with the natural curvature and shape of the female anatomy, and specifically with the female external genitalia (illustrated in FIG. 3), and includes a top contact surface 12 for contacting with the user's irritated external genitalia when inserted properly, i.e. with the surface 12 facing the user. A bottom surface 14 of the insert defines a flange 16, which is preferably slightly curved and relatively thin and faces the underwear of the user during use. The top contact surface 12 includes a ridge 18 that rises from the flange 16. The ridge 18 is raised above the level of the flange 16 and is smaller and narrower than the flange 16 as seen from the top (see FIG. 2), and like the flange 16 has the general shape of an inverted tear drop. As best seen in FIG. 1, the ridge 18 can include a rounded crest 20 that is the highest point above the flange 16. The ridge 18 tapers from the crest 20 towards the anterior end 22 and posterior end 24 of the flange 16. As can be appreciated from viewing FIG. 1, the slope of the ridge 18 as it tapers from the crest 20 towards the anterior end 22 is steeper than the slope as it tapers towards the posterior end 24.

Each of the labial inserts typically includes the top contact surface 12 for contacting the female external genitalia, the bottom surface 14 defining the flange 16, which in turn has an anterior end 22 and a posterior end 24 and a curvature from the anterior end to the posterior end in order to conform to the user's anatomy. In addition, the top contact surface 12 typically includes the ridge 18 raised above the level of the flange and having the rounded crest 20 at the highest point above the flange 16. As can be appreciated from viewing FIG. 1, the ridge 18 includes a first tapered portion sloping from the rounded crest 20 towards the anterior end 22 of the flange, and a second tapered portion sloping from the rounded crest 20 towards the posterior end 24 of the flange. The slope of the first tapered portion is typically steeper than the slope of the second tapered portion, as seen in FIG. 1.

Figure 3:
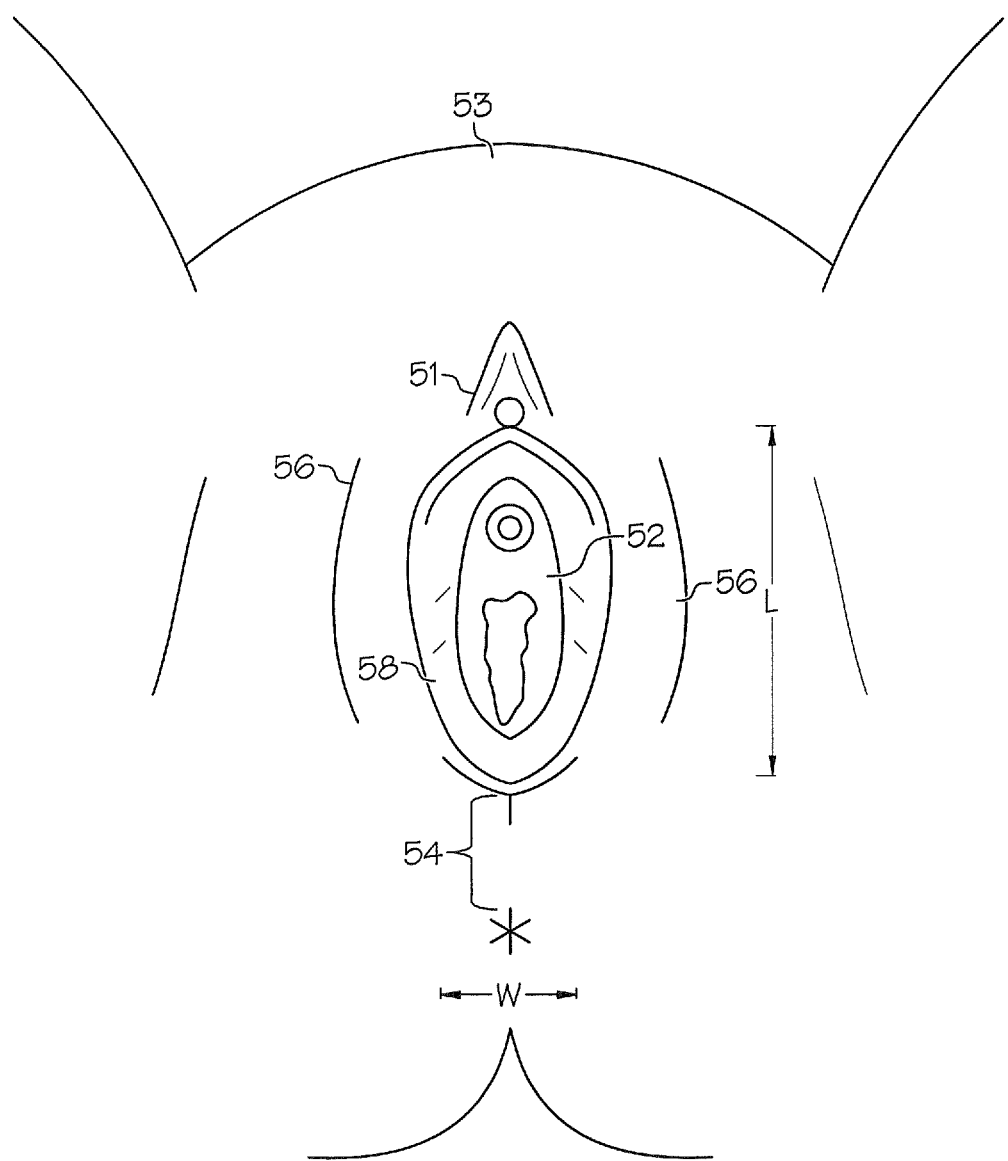
FIG. 3 illustrates the external genitalia of a typical human female.

FIG. 3 illustrates the anatomy of the external female genitalia. The specific anatomy of the female user determines the length L of the labial insert 10 (of FIGS. 1 and 2). More specifically, the labial insert 10 is configured to generally span the length between the female user's clitoris 51 and perineum 54. The width W of the insert is also determined by the user's specific anatomy, and is intended to allow insertion of the labial insert 10 between the user's labia majora 56, so that the top surface 12 makes soothing contact with the inflamed tissues of the female vulva. The tissues of the female vulva shown in FIG. 3 include the clitoris 51, the vestibule 52, the perineum 54, and the labia minora 58, in addition to the labia majora 56. The vestibule 52 is located between or within the labia majora 56 and labia minora 58. The labia majora 56 are two prominent longitudinal skin folds which extend downward and backward from the mons pubis 53 to the perineum 54, and are commonly known as the "outer lips".

Regarding dimensions, the length L of the labial insert 10 is typically between 25 mm to 110 mm in length (1.0 inches to 4.0 inches), and preferably between 35 mm and 75 mm (1.4 inches to 3 inches). The width W of the insert is typically between 10 mm to 75 mm (0.4 inches to 3 inches), and preferably between 20 mm and 30 mm (0.8 inches to 1.2 inches). The typical height for the tapered portion of the ridge 18 above the flange 16 is between 5 mm and 70 mm (0.2 inches to 2.75 inches), with the crest 20 being between 10 and 75 mm (0.4 inches to 3.0 inches) above the flange 16. It is also preferable, although not required, that flange 16 have a curvature from the top or anterior end 22 to the bottom or posterior end 24 in order to conform more closely to the user's anatomy.

Although these dimensions are provided as typical or representative examples, these dimensions are not intended to be limiting. One of skill in the art will appreciate that there is a wide range of variation among women with respect to the relative size and shape of the external female genitalia. The size of a particular user's anatomy can depend on the size and age of the woman, as well as the woman's race. As such, a larger or smaller insert 10 than the exemplary dimensions described above may be desired, due to the user's specific anatomy, in order to produce a comfortable and effective fit. Preferably the insert 10 can be custom-fit, for example via a mold of each user's vulva, to allow the labial insert 10 to be in close and comfortable physical contact with the inflamed and irritated area. As a result, any dimensions that meet the objectives of this invention are within the scope of the invention.

Further, although the insert 10, including the flange 16 and ridge 18, is shown herein having an inverted tear drop shape, it is not required to have that particular shape. Rather, the insert 10 may have a constant diameter or increasing or decreasing diameter going from the anterior end 22 to the posterior end 24. Further, the flange 16 may be curved or straight as desired to give the most comfortable and effective fit between the contact surface 12 and the external female genitalia. In use, the ridge 18 of the insert is typically not inserted into the user's vagina, and only makes contact with the external female genitalia shown in FIG. 3.

The labial insert 10 may be constructed so that the flange 16 and the ridge 18 are integrally formed, or they may be made separately and then attached together by means well known in the art, including but not limited to adhesives, heat sealing, frictional fit, threaded connection, and other mechanical attachment means. The ridge 18 preferably protrudes from the flange 16 at an angle that provides the best contact between the top contact surface 12 and the external female genitalia, to provide the utmost comfort and effectiveness for an individual female user. A key function of the labial insert 10 is to cool the irritated external female genitalia and thus provide maximum benefit and relief to the user. Consequently, the labial insert 10 must be made of a material that is capable of being cooled and remaining cold during use. In one embodiment, the material of insert 10 has a high heat capacity so that once the insert is cooled prior to use, as will be described hereafter, it will remain cool during the time required for relief.

The labial insert 10, including the flange 16 and ridge 18, can be entirely made of a single solid material, or the insert can be hollow inside with a cooling material maintained within the outer surface of the insert. If the insert is entirely made of a single solid material, it is preferably made of a hard, smooth plastic having a high heat capacity such as polyvinyl chlorides (PVC), high-density polyethylene (HDPE), or ethylene-vinyl acetate (EVA). In this embodiment the flange 16 and the ridge 18 may be integrally formed by methods such as molding or forming, or may be separately made by such methods and joined together as described above.

If the insert is hollow inside with a cooling material maintained within the outer surface of the insert, the cooling material can be a gel having a large thermal mass to help maintain the insert at the desired operating temperature. This can allow the insert to remain cool for an extended period of time, since it requires a large amount of heat to increase its core temperature. The thermal mass of the gel is affected by the volume of gel material included, as well as the type of gel material. Also, the amount of heat that may be absorbed during use is affected by the initial temperature of the gel in addition to its thermal mass. Exemplary materials for such a cooling gel material can include methyl cellulose gels, hydrogels such as agar hydrogels, gelatin gels, and polyvinyl alcohol gels.

Figure 4:
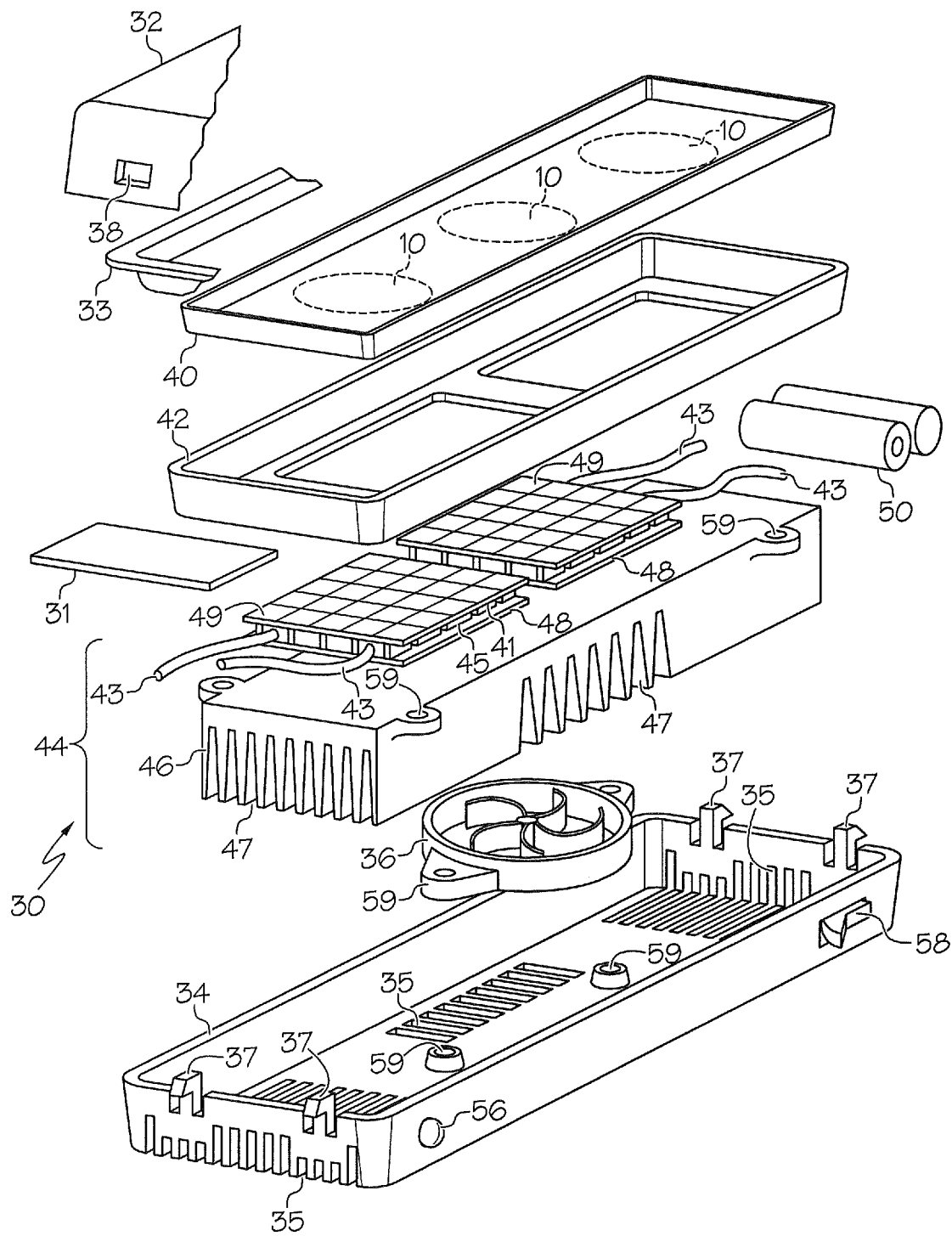
FIG. 4 is a perspective view of a preferred embodiment of a portable cooling unit according to the present invention.

FIG. 4 shows a preferred embodiment of a lightweight and portable cooling unit or container 30, in combination with the labial inserts 10 described above. The cooling unit 30 incorporates an upper housing 32 and a base housing 34. The base housing 34 incorporates air inlet/outlet vents 35 for a fan 36 contained in the base housing. The base housing 34 can be reversibly secured to the upper housing via clips 37 projecting from the base 34, which can be inserted or otherwise fit through clip holes 38 in the upper housing 32. Other connecting means can be used, as are known in the art. A power switch 58 turns on the unit 30, which is indicated by an LED/Power button 56, and the user can control operation of the unit 30 via an interactive printed circuit board 31, as is known in the art.

The embodiment of the cooling unit 30 shown in FIG. 4 is particularly adapted to hold three labial inserts 10, which are seated within a cooling compartment or plate 40, which in turn is seated within an insulating tray 42. A rubber sealing layer 33 is located between the upper housing 32 and the cooling compartment 40, and serves to insulate the unit and prevent loss of cooling energy when the unit 30 is closed, and can also ensure that thermal energy is not transferred from the cooling compartment 40 to the cover 32. A thermoelectric heat transfer module 44 (i.e., a Peltier effect module) is directly beneath and in thermally conductive communication with the cooling compartment 40. Briefly, thermoelectric cooling uses the Peltier effect (also called the thermoelectric effect) to create a heat flux between two different types of materials; specifically, semiconductors 41, 45 having different electron densities are connected side by side with one another and sandwiched between upper and lower ceramic plates 48, 49, respectively. The semiconductors 41, 45 are then connected electrically in series via circuitry 43 and a battery 50. When a voltage is applied, the current generated between the semiconductors causes a temperature difference. The thermoelectric effect module 44 transfers heat from one side of the device to the other, with consumption of electrical energy, depending on the electrical current direction. It can be used either for heating or for cooling, although in practice the main application is cooling.

The heat transfer module 44 creates a "cold side" above upper plates 49 and a "hot side" below lower plates 48. The hot side is immediately adjacent to a heat sink 46, so that the lower plates 48 transfer thermal energy to the heat sink 46, allowing the hot side to essentially remain at ambient temperature, while the cold side (in contact with the cooling compartment 40) loses heat and drops below room temperature. The heat sink 46 includes ductwork 47 which serves to channel air to the fan 36. Thermal energy (heat) from the heat sink 46 is removed from the cooling unit 30 by action of the fan 36, which is powered by the batteries 50 to expel the hot air passing through the air vents 35 to the ambient surroundings. Small screws (not shown) are intended to run through holes 59 passing through the base 34, the fan 36 and the heat sink 46 to hold and or sandwich these elements together, ensuring good thermally transmissive contact between them. When heat is actively removed below the hot side of the heat transfer module 44, the cooling compartment 40 is cooled to a desired temperature, which in turn cools the inserts 10.

The printed circuit board 31 as presented in FIG. 4 includes and/or is connected to a small microprocessor (not shown), which itself includes and receives input from a resistance temperature detector as is known in the art to control the amount of voltage delivered to the heat transfer module 44 and the fan 36. The circuit board 31 including the microprocessor and temperature detector can be located within the base housing 34. The microprocessor can control the heat transfer module 44 via a variable voltage output programmed into the microprocessor at the time of assembly. The voltage output can be varied by the microprocessor in response to signals from the temperature detector. The power supplied to the module 44 by the microprocessor can be only as much as is required to maintain proper temperature in the cooling compartment 40. This facilitates extended use of a portable battery 50 to power the unit when other power sources are not available.

In use, the microprocessor, via user activation of the circuit board 31, activates the thermoelectric heat transfer module 44. The heat transfer module 44 cools the cooling compartment of plate 40 to a target temperature. Because the inserts 10 are in adjoining, thermally conductive communication with the cooling plate 40, the inserts 10 are cooled via conduction, so that the cool temperature of the module 44 is transferred to the adjoining plate 40, which is then transferred to the inserts 10 as they sit on the surface of the cooling plate 40. Ideally the cooling plate 40 and the inserts 10 attain thermal equilibrium, but there may be a lag in time before this happens. For example, the cooling compartment 40 may reach the target temperature in about ten minutes, but it may take a few minutes longer for the inserts 10 to reach the target temperature. The insulating tray 42 minimizes thermal loss from the cooling compartment 40 to the ambient surroundings. The microprocessor can also operate the fan 36 to cool the heat sink 46 and draw away heat extracted from the cooling plate 40 and the inserts 10.

The cooling unit 30 provides a means to cool the labial inserts 10, which are re-useable and can be used successively, one at a time, if needed. The desired operating/target temperature of the labial inserts may vary from one individual to the next, and from one use to the next. This target temperature is desirably less than room temperature (i.e. less than 20 degrees Celsius or 70 degrees Fahrenheit) and greater than a temperature that may cause cold injury or frostbite (i.e. greater than 0 (zero) degrees Celsius or 32 degrees Fahrenheit). It is also desirable to maintain the cooling insert at a relatively constant operating temperature over an extended period of time. The portable cooling unit 30 can be used for both cooling and transporting either one or a plurality of the labial inserts, and the labial inserts can be applied when needed to the external female genitalia for treatment of vulvar inflammation.

Once an insert 10 is cooled to the desired target temperature, the insert is placed in the vulva between the labia majora (56, see FIG. 3). When this is done, the ridge 18 will come into contact with the user's vulva between the labia. The crest 20 of the ridge 18 conforms to the user's anatomy to bring the cooled contact surface 12 into intimate contact with the affected area. If the insert 10 eventually ceases to be cool enough to provide the desired therapeutic benefit or comfort, the user may remove it and replace it with another. Each insert 10 is reusable, and thus may be placed back in the cooling unit 30 (preferably after cleaning) to be re-cooled or and thereafter re-used. The combination of the cooling unit 30 and a plurality of inserts 10 can continue to provide beneficial cooling of the external female genitalia for an extended period of time. While primarily intended for human use, the inventive apparatus and method can be adapted for use in animals as well for treating vulva-related burning and itching.

While the present invention has been illustrated by the description of embodiments and examples thereof, it is not intended to restrict or in any way limit the scope of the appended claims to such detail. Additional advantages and modifications will be readily apparent to those skilled in the art. Accordingly, departures may be made from such details without departing from the scope of the invention.

What is claimed is:

1. An apparatus for providing immediate relief from burning and itching of the female external genitalia, the apparatus comprising:
   a) a cooling unit, the cooling unit comprising:
      i. an upper housing for accommodating:
         i) a cooling compartment for receiving the one or more labial inserts;
         ii) an insulating tray; and
         iii) a sealing layer, wherein the cooling compartment is seated within the insulating tray and the sealing layer is placed between the upper housing and the cooling compartment;
      2) a base housing for accommodating:
         i) inlet air vents;
         ii) outlet air vents; and
         iii) a fan; and
      3) a thermoelectric heat transfer module for placement between the upper housing and the base housing, wherein the heat transfer module is in thermally conductive communication with the cooling compartment; and
   b) one or more labial inserts, wherein the cooling unit is portable and operable to cool the one or more labial inserts to a desired target temperature, and wherein each of the one or more labial inserts can be applied to the external female genitalia of a user to maintain a controlled temperature to the affected area for an extended period of time.

2. The apparatus of claim 1, wherein each of the one or more labial inserts includes: i) a top contact surface for contacting the female external genitalia; (ii) a bottom surface defining a flange having an anterior end and a posterior end, wherein the flange has a curvature from the anterior end to the posterior end in order to conform to the user's anatomy.

3. The apparatus of claim 2, wherein the top contact surface includes a ridge raised above the level of the flange, the ridge including a rounded crest at the highest point above the flange, a first tapered portion sloping from the rounded crest towards the anterior end of the flange, and a second tapered portion sloping from the rounded crest towards the posterior end of the flange.

4. The apparatus of claim 3, wherein the length of each of the one or more labial inserts from the anterior end to the posterior end of the flange is between 25 mm and 110 mm, wherein the width of each of the one or more labial inserts is between 10 mm and 75 mm and, wherein the height for the first and second tapered portions is between 5 mm and 70 mm above the flange, and wherein the height of the crest is between 10 mm and 75 mm above the flange.

5. The apparatus of claim 3, wherein the slope of the first tapered portion is steeper than the slope of the second tapered portion.

6. The apparatus of claim 2, wherein each of the one or more labial inserts are configured for placement between the user's labia majora so that the top contact surface makes contact with the external female genitalia.

7. The apparatus of claim 2, wherein the flange has the shape of an inverted tear drop from the anterior end to the posterior end.

8. The apparatus of claim 3, wherein the labial insert is constructed so that the flange and the ridge are integrally formed.

9. The apparatus of claim 1, wherein the base housing is reversibly secured to the upper housing via clips projecting from the base housing for insertion through clip holes in the upper housing.

10. The apparatus of claim 1, wherein the cooling compartment receives three labial inserts.

11. An apparatus for providing immediate relief from burning and itching of the female external genitalia, the apparatus comprising:
   a) a cooling unit, wherein the cooling unit comprises:
      i) an upper housing for accommodating:
         1) A cooling compartment for receiving the one or more labial inserts;
         2) An insulating tray; and
         3) a rubber sealing layer, wherein the cooling compartment is seated within the insulating tray and the rubber sealing layer is placed between the upper housing and the cooling compartment;
      ii) a base housing for accommodating:
         1) Inlet air vents;
         2) Outlet air vents; and
         3) a fan; and
      iii) a thermoelectric heat transfer module for placement between the upper housing and the base housing, wherein the heat transfer module is in thermally conductive communication with the cooling compartment, and wherein the base housing is reversibly secured to the upper housing with the thermoelectric heat transfer module secured in between; and b) one or more labial inserts, wherein each of the one or more labial inserts includes:
   i) a top contact surface for contacting the female external genitalia, wherein the top contact surface includes a ridge raised above the level of the flange, the ridge including a rounded crest at the highest point above the flange, a first tapered portion sloping from the rounded crest towards the anterior end of the flange, and a second tapered portion sloping from the rounded crest towards the posterior end of the flange; and
   ii) a bottom surface defining a flange having an anterior end and a posterior end, wherein the flange has a curvature from the anterior end to the posterior end in order to conform to the user's anatomy, wherein the cooling unit is portable and operable to cool the one or more labial inserts to a desired target temperature, and wherein each of the one or more labial inserts can be applied to the external female genitalia of a user to maintain a controlled temperature to the affected area for an extended period of time.

12. The apparatus of claim 11, wherein the length of each of the one or more labial inserts from the anterior end to the posterior end of the flange is between 25 mm and 110 mm, wherein the width of each of the one or more labial inserts is between 10 mm and 75 mm, wherein the height for the first and second tapered portions is between 5 mm and 70 mm above the flange, and wherein the height of the crest is between 10 mm and 75 mm above the flange.

13. The apparatus of claim 11, wherein the slope of the first tapered portion is steeper than the slope of the second tapered portion.

14. The apparatus of claim 11, wherein each of the one or more labial inserts are configured for placement between the user's labia majora so that the top contact surface makes contact with the external female genitalia.

15. The apparatus of claim 10, wherein the flange has the shape of an inverted tear drop from the anterior end to the posterior end.

16. A method for providing immediate relief of female burning and itching, the method comprising:
   a) providing an apparatus for both cooling and transporting one or more labial inserts, the apparatus comprising:
      i) a cooling unit, the cooling unit comprising:
         i. an upper housing for accommodating: a cooling compartment for receiving the one or more labial inserts, an insulating tray, and a sealing layer, wherein the cooling compartment is seated within the insulating tray and the sealing layer is placed between the upper housing and the cooling compartment
         2) a base housing for accommodating: inlet air vents, outlet air vents, and a fan; and
         3) a thermoelectric heat transfer module for placement between the upper housing and the base housing, wherein the heat transfer module is in thermally conductive communication with the cooling compartment and ii) one or more labial inserts, wherein each of the one or more labial inserts includes a top contact surface for contacting the female external genitalia;
   b) cooling the one or more labial inserts to a desired target temperature within the cooling unit;
   c) removing one of the one or more labial inserts from the cooling unit when it reaches the desired target temperature; and
   d) inserting one of the cooled one or more labial inserts between a user's labia majora so that the top contact surface makes contact with the external female genitalia of a user to maintain a controlled temperature to the external genitalia for an extended period of time.

17. The method of claim 16, wherein each of the one or more labial inserts further includes a bottom surface defining a flange having an anterior end and a posterior end, wherein the flange has a curvature from the anterior end to the posterior end in order to conform to the user's anatomy.

18. The apparatus of claim 17, wherein the top contact surface includes a ridge raised above the level of the flange, the ridge including a rounded crest at the highest point above the flange, a first tapered portion sloping from the rounded crest towards the anterior end of the flange, and a second tapered portion sloping from the rounded crest towards the posterior end of the flange.

* * * * *

UNITED STATES PATENT AND TRADEMARK OFFICE
CERTIFICATE OF CORRECTION

| | |
|---|---|
| PATENT NO. | : 11,590,021 B2 |
| APPLICATION NO. | : 16/503842 |
| DATED | : February 28, 2023 |
| INVENTOR(S) | : Kesha Williams |

It is certified that error appears in the above-identified patent and that said Letters Patent is hereby corrected as shown below:

In the Claims

Claim 4, Column 8, Line 22, delete "mm and, wherein" and insert --mm, wherein--.

Claim 15, Column 9, Line 37, delete "claim 10" and insert --claim 11--.

Signed and Sealed this
Fourth Day of April, 2023

*Katherine Kelly Vidal*

Katherine Kelly Vidal
*Director of the United States Patent and Trademark Office*